(12) United States Patent (10) Patent No.: US 8,211,177 B2
Richelsoph (45) Date of Patent: Jul. 3, 2012

(54) LOAD SHARING INTERBODY FUSION DEVICE

(75) Inventor: Marc E. Richelsoph, Belmont, GA (US)

(73) Assignee: Intelligent Implant Systems, Charlotte, NC (US)

( * ) Notice: Subject to any disclaimer, the term of this patent is extended or adjusted under 35 U.S.C. 154(b) by 615 days.

(21) Appl. No.: 12/329,893

(22) Filed: Dec. 8, 2008

(65) Prior Publication Data

US 2009/0157187 A1  Jun. 18, 2009

Related U.S. Application Data

(60) Provisional application No. 61/007,385, filed on Dec. 12, 2007.

(51) Int. Cl.
*A61F 2/44* (2006.01)
(52) U.S. Cl. ................................... 623/17.16
(58) Field of Classification Search .... 623/17.11–17.16; 606/60, 246
See application file for complete search history.

(56) References Cited

U.S. PATENT DOCUMENTS

| 6,419,705 | B1 * | 7/2002 | Erickson | 623/17.16 |
| 6,569,201 | B2 * | 5/2003 | Moumene et al. | 623/17.11 |
| 7,115,146 | B2 * | 10/2006 | Boyer et al. | 623/23.63 |
| 2007/0260324 | A1 * | 11/2007 | Joshi et al. | 623/23.51 |

* cited by examiner

*Primary Examiner* — Eduardo C Robert
*Assistant Examiner* — Ellen C Hammond
(74) *Attorney, Agent, or Firm* — Kohn & Associates, PLLC

(57) ABSTRACT

The present invention is a load sharing intervertebral fusion device that allows for reconstruction of the proper disc space between two vertebral bodies while allowing bone material packed within the fusion device to share loading and stress for enhanced healing. The device includes two sections, an upper and lower section, separated by a bioresorbable spacer. The upper section slides relative to the lower section with the bioresorbable material being placed in load therebetween. The upper section and lower sections are effectively held apart, creating an initial fixed spacer for implantation of the intervertebral disc space. Openings in the implant construct allow for bone graft and bone substitutes to be placed within the implant to allow for fusion through the implant construct. After implantation and over a period of time based on bone resorbtion and remodeling, the spacer resorbs, thereby maintaining load on the bone graft material.

15 Claims, 9 Drawing Sheets

LOAD SHARING INTERBODY FUSION DEVICE

CROSS-REFERENCE TO RELATED APPLICATIONS

This application claims the benefit of priority to U.S. Provisional Ser. No. 61/007,385, filed Dec. 12, 2007, which is incorporated herein by reference.

TECHNICAL FIELD

The present invention relates generally to intervertebral fusion devices, and more specifically it relates to a load sharing intervertebral fusion device which assists in fusing two vertebrae.

BACKGROUND OF THE INVENTION

Intervertebral body spacers have been in use for many years. Typically, these spacers are constructed from polymers, such as polyetherether ketone (PEEK) polymer, titanium, and stainless steels. By inserting these devices into a disc space, restoration of the disc space height is reestablished. The device removes pressure on nerve structures and eliminates nerve entrapment caused by the otherwise collapsed disc space. More recently developed devices, constructed of polymers or composites, provide an additional benefit of being radiolucent when viewed by xray techniques.

The most significant problem of the aforementioned conventional intervertebral body spacers is that the rigidity of the spacer does not allow for load sharing with a bone graft or bone substitute. Such grafts are disposed in the intervertebral space in order to fuse the vertebral surfaces that define the space together. The aforementioned prior art devices cannot fuse the vertebrae together alone, so bone, bone substitutes, and bone morphogenetic protein (BMP) type materials are used to provide a means of bone fixation. However, Wolff's law states that bone grows along lines of stress. For good fusion to occur, the implant spacer must distribute a load to the graft. Another problem with conventional spacers that are made from bioresorbable materials, such as poly-L-lactides (PLLA), is that these materials have limited strength and are designed to resorb completely away. With limited strength, these devices can fracture under the high loads of the spine.

In addition to the above, fusion in vivo is a variable process. It may happen quickly, slowly, or not at all due to a variety of other reasons characteristic of the intervertebral space. If fusion does not take place and the bioresorbable materials resorb, the space established during surgery closes and the preoperative painful condition returns.

While the aforementioned devices can be suitable for a particular purpose to which they address, they are not as suitable to providing a device that permits load sharing with the bone graft or bone substitute material while providing sufficiently rigid support of the spine during a healing process. In contradistinction, the present invention provides an apparatus primarily developed for the purpose of creating controlled load sharing while providing sufficiently rigid support of a spinal implant system and preventing full collapse of the disc space should a fusion fail to occur.

SUMMARY OF THE INVENTION

In accordance with the present invention, there is provided an interbody fusion device including body means for spacing apart opposing vertebral surfaces when the body means is implanted therebetween and bone graft load sharing means for sharing the loads, placed on the body means by the opposing vertebral surfaces, between the body means and bone graft material contained by the body means.

The present invention further provides a method of spacing apart opposing vertebral end plates by inserting a spacer between opposing vertebral end plates and controlling reduction and height of the spacer during a healing process of a reconstructed vertebral space defined by the end plates.

The present invention further provides an interbody fusion device including a first portion including a first side having a first end plate surface for engaging an end plate of a first vertebral body and a second opposite side having a male portion extending therefrom. The male portion includes an end surface. A second portion includes a second end plate surface for engaging an opposing end plate of a second vertebral body. The second portion includes a cavity defined by a wall portion surrounding a floor portion for slidingly receiving the male portion therein and entrapping a bioresorbable material between the end surface and the floor portion.

The present invention also provides an interbody fusion device including piston means for entrapping a bioresorbable material therein and having a predetermined height which reduces as the bioresorbable material resorbs. Vertebral end plate gripping means fixedly engages opposing vertebral end plates when the device is disposed therebetween.

The present invention also includes an interbody fusion device including a male member including a first end plate surface for engaging an end plate of a first vertebral body and a lower surface. A female member includes a second end plate surface for engaging an opposing end plate of a second vertebral body. The female member includes a cavity having wall portions surrounding a floor portion for slidingly receiving the lower surface therein and entrapping a bioresorbable material between the lower surface and the floor portion.

The present invention further provides a method of spacing apart opposing vertebral surfaces by entrapping a bioresorbable material within a piston body having a predetermined height and fixedly engaging the piston between opposing vertebral end plates. The height of the piston is reduced as the bioresorbable material resorbs.

The present invention also provides a method of fusing together opposing intervertebral surfaces by implanting a body between opposing vertebral surfaces and maintaining spacing between the opposing vertebral surfaces as the opposing vertebral surfaces place a load on the body. The load is shared between the body and bone graft material contained by the body.

Finally, the present invention provides a method of remodeling vertebral bone by containing a column of bone graft material in a body member having a reducible height while exposing ends of the column. The body member is inserted between opposed vertebral end plates. The height of the body member decreases over time to load the column of bone graft material over time.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
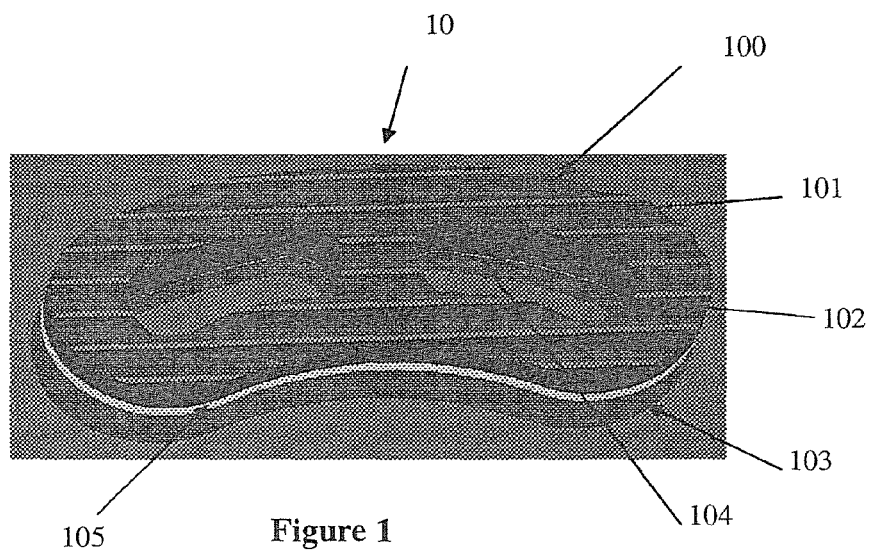
FIG. 1 is a perspective view of the present invention in kidney shaped form.
Figure 2:
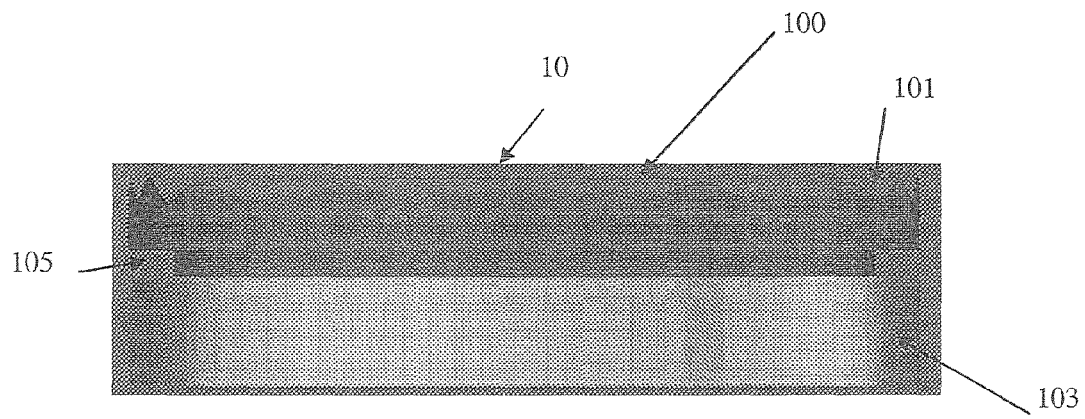
FIG. 2 is a side view of the present invention in a fully opened position.
Figure 3:
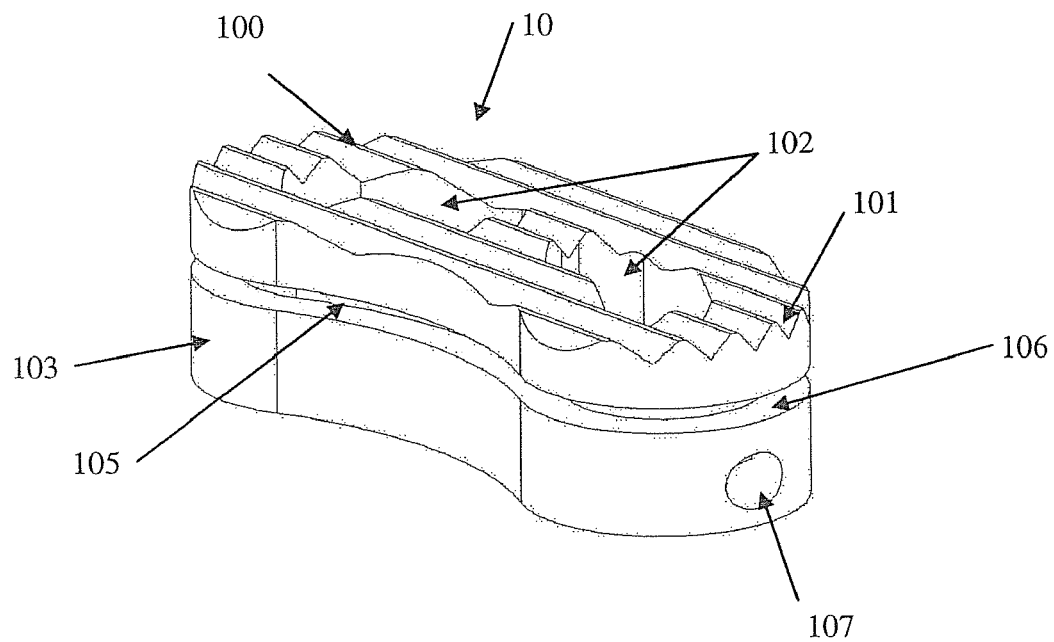
FIG. 3 is a side perspective view of the present invention.
Figure 4:
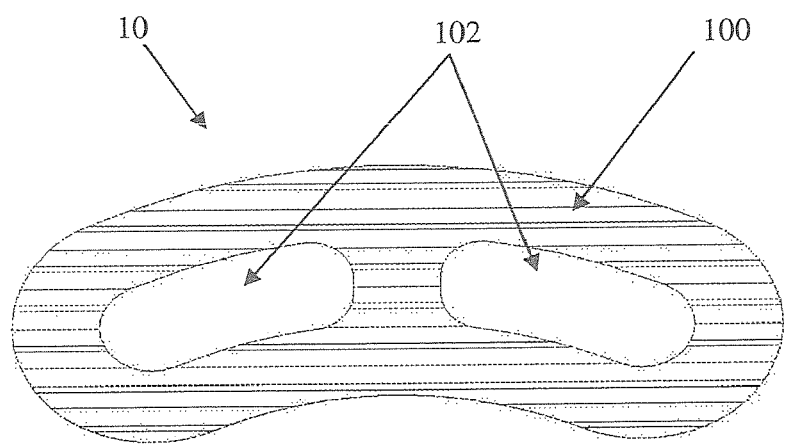
FIG. 4 is a top plan view of the present invention.
Figure 5:
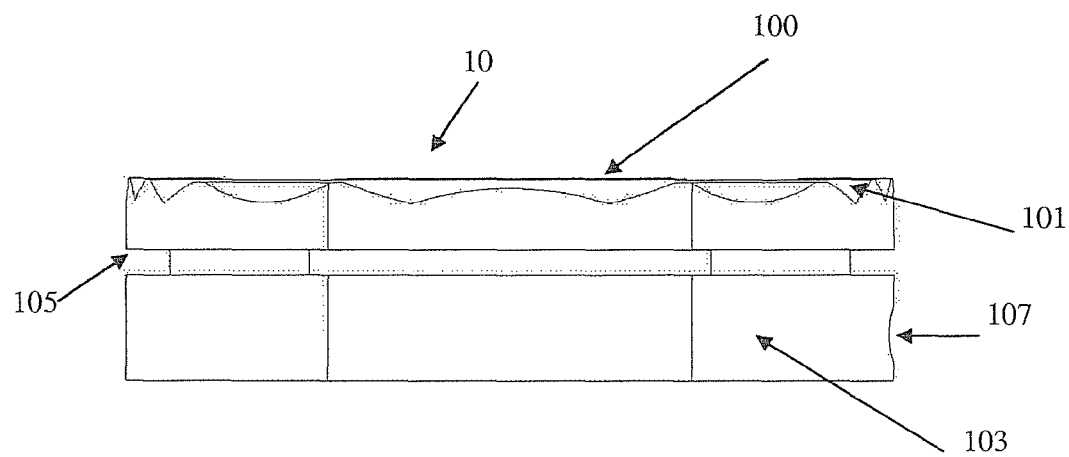
FIG. 5 is an elevational side view of the present invention.

An interbody fusion device made in accordance with the present invention is generally shown at 10 in the Figures. The device 10 generally includes an upper body section 100 which moves relative to a lower body section 103. Together, the upper and lower body sections 100, 103 provide a body mechanism for spacing apart opposing vertebral surfaces when the body mechanism is implanted therebetween. The invention is characterized by including a bone graft load sharing mechanism for sharing loads, placed on the body portions 100, 103 by the opposing vertebral surfaces, the loads being shared between the body portions 100, 103 and bone graft material contained by the body portions 100, 103. That is, loads are placed on the device 10 by the surrounding vertebral end plates that define the intervertebral space into which the device 10 is surgically placed. In prior art devices, the loads placed on the device would be totally isolated from any bone graft material contained therein. The present invention provides a device wherein loads placed on the device are shared with the bone graft material contained therein. Significantly, this induces a successful fusion as explained below.

Mechanistically, the healing process is one of remodeling, replacement, and resorption of bone. The bone or bone substitute material is not alive, and in the case of autogenous bone, it is not alive either once the bone is taken from its initial location. The bone acts as a source of calcium, minerals, and structure for the cells to restructure. In a successful fusion wherein the bone graft fuses with the vertebral body end plates which define the intervertebral space, the non-living material is replaced by living bone. In view of this biology, the general purpose of the present invention is to provide a load sharing intervertebral fusion device that has many of the advantages of the interbody fusion spacers of the prior art, and many novel features that results in a new load sharing intervertebral fusion device.

Figure 10:
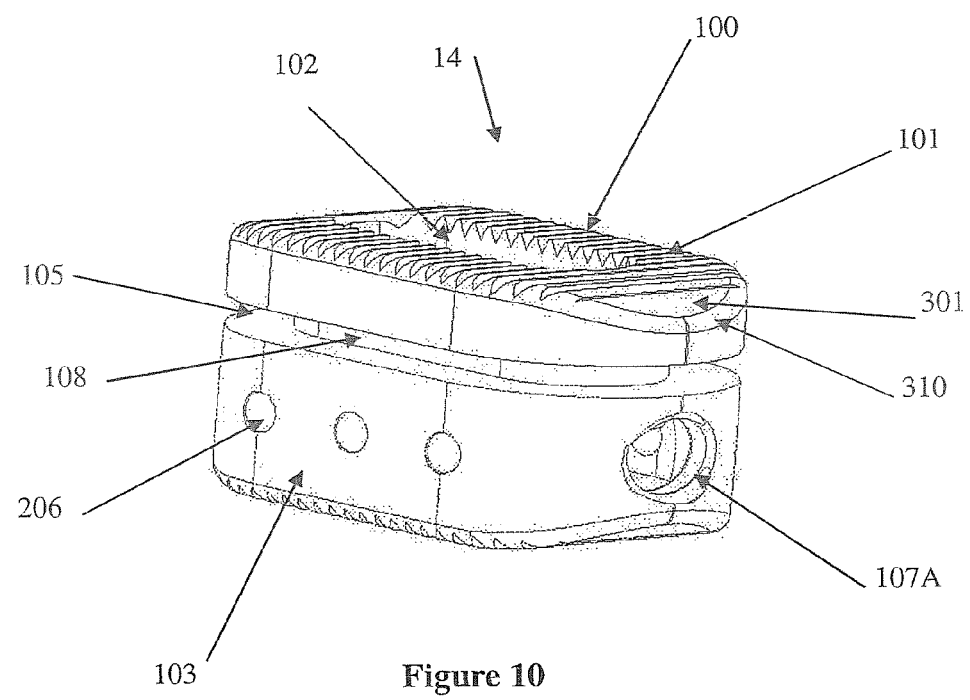
FIG. 10 is a side perspective view of a rectangular embodiment of the present invention.
Figure 11:
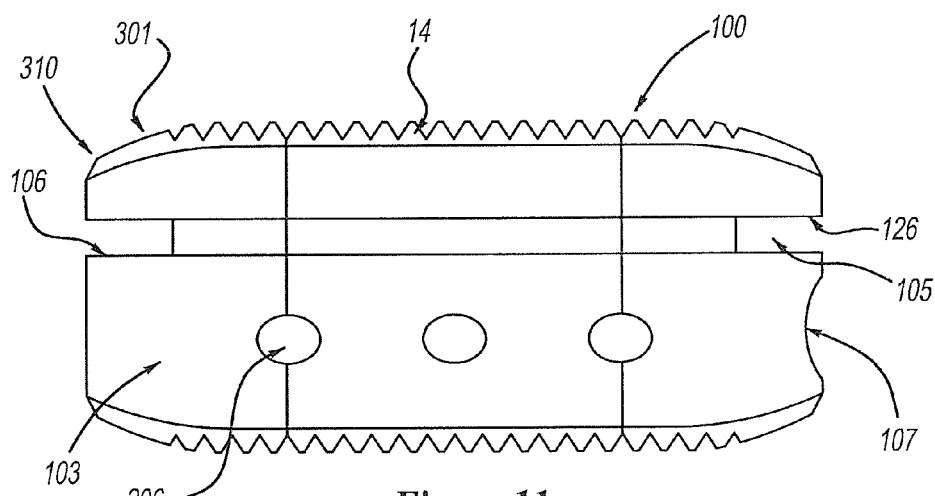
FIG. 11 is an elevational side view of the rectangular embodiment of the present invention.

As shown in FIG. 1, the body portions 100, 103 can be constructed in various shapes, depending upon the face into which it is inserted. In FIG. 1, the device is shown at 10 in a kidney shape. Another preferred shape is rectangular, which is shown at 14 in FIG. 10 et seq.

In order to facilitate engagement of the device 10 with the surrounding vertebral end plates, upper and lower sections 100, 103 have a roughened surface 101. The roughened surface can be in the form of grooves with a saw tooth type groove, V groove, slots, or other textured surfaces formed or machined into the upper and lower sections 100, 103. The grooves can also be at angles relative to one another, such that the upper section 100 grooves can be perpendicular to the grooves on the lower section 103. In other words, the grooves 101 on the upper and lower body portions 100, 103 can cooperate to assist in fixedly securing the position of the device 10 within the intervertebral space.

In order to allow bone to grow inside of the implant device 10, bone graft chambers 102 define openings from the upper section 100 through the lower section 103. These chambers 101 can be filled with autogenous or allograft bone, bone substitutes, BPM type materials, or combinations thereof.

The chambers filled with the autogenous or allograft bone or other BPM type material create a column of bone material between the upper and lower vertebral bodies to assist in fusing the vertebrae together. In order to maintain a load on the column of bone-like material, the present invention includes a height reducing mechanism. To achieve the height reduction of the effective height of the combined body members 100, 103, a bioresorbable spacer 104 is sandwiched between the upper section 100 and the lower section 103. The thickness of the bioresorbable spacer 104 can be varied depending upon the thickness originally desired for the device 10 at its maximum height.

As shown in the various figures, the bioresorbable spacer also includes holes 113 to allow for the packing bone materials to extend at a column throughout the implant device 10. By utilizing the bioresorbable spacer 104 between the upper section 100 and lower section 103, the height of the implant is effectively set and rigid at the time of implantation, but over time, the bioresorbable spacer 104 resorbs. This allows the implant device 10 to maintain loading on the bone material in the form of the columns within the chambers 102, 113 to be constantly loaded.

As previously discussed, stress on the column of bone material is necessary as Wolff's Law states that the bone will grow along lines of stress. The present novel design allows the implant device 10 to be inserted into the disc space to reestablish the proper disc space, but not act as a rigid spacer. Accordingly, the present invention allows for better bone healing.

As the bioresorbable spacer 104 has a set thickness predetermined prior to insertion, and is placed between the upper section 100 and lower section 103, the thickness of the spacer controls exactly how much reduction in height of the overall implant device 10 is allowed during the healing process and creates a gap 105 between the upper and lower sections 100, 103. This construction creates a safety feature of the present invention, such that under the possibility that bone quality does not permit healing and a successful fusion, once the bioresorbable spacer 104 is completely resorbed, the upper section lip 126 contacts the lower section lip 106 thereby preventing any further vertical movement between the upper and lower sections 100, 103. Thus, if healing fails, a spacer holding the vertebrae apart and off the nerve roots still exists.

Specific examples of such bioresorbable materials include polyesters, poly (amino acids), polyanhydrides, polyorthoesters, polyurethanes, polycarbonates and copolyesters of Σ-caprolactone, trimethylene carbonate, and paradioxanone.

The polyester can be selected from the group of homopolymers and copolymers of poly(lactic acid) (PLLA) and poly(glycolic acid) (PLGA). Such bioresorbable polymers are capable of safely existing in the body and eventually absorbing without causing harm or adverse interactions. It has been found that such bioresorbable polymers have the ability to safely remain in the body for controlled lengths of time which has made them particularly suitable for various medical applications including those of the present invention.

Figure 6:
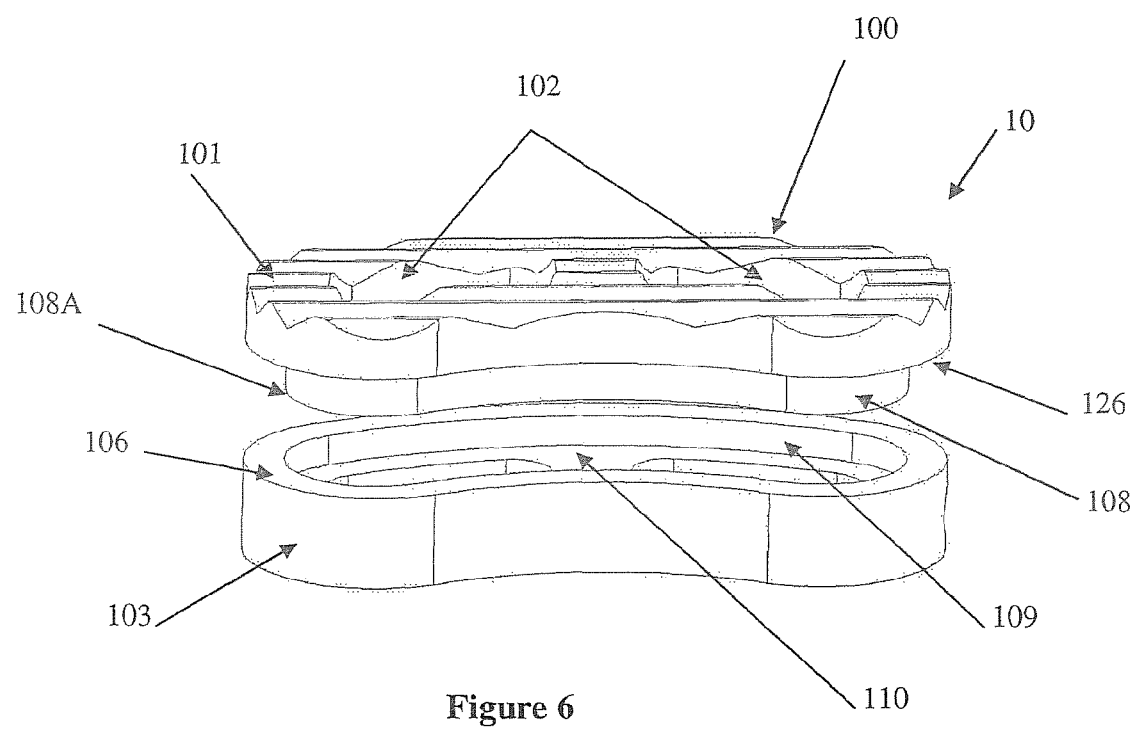
FIG. 6 is an exploded side perspective view of the present invention.
Figure 7:
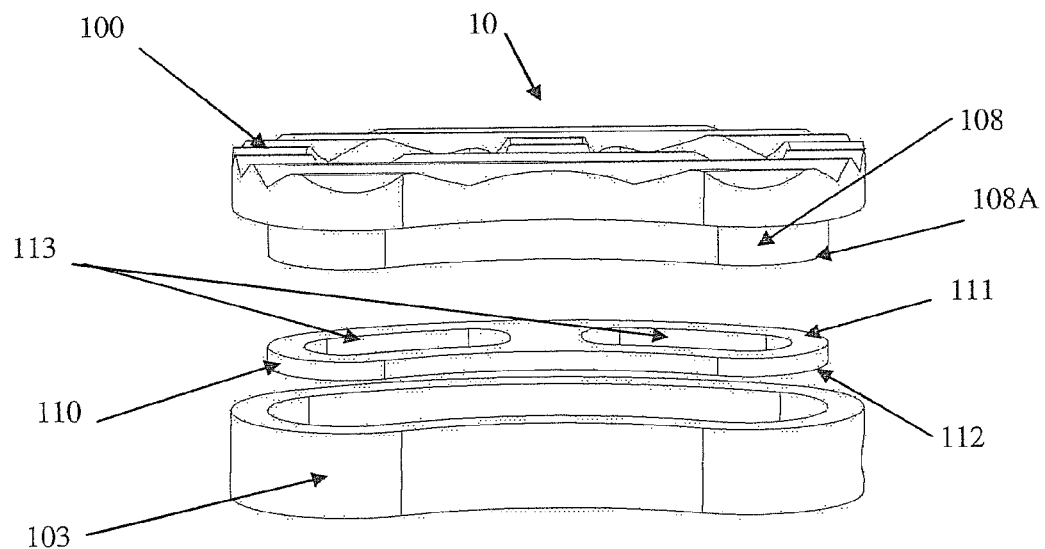
FIG. 7 is an exploded side perspective view of present invention showing a bioresorbable spacer.

FIGS. 6 and 7 provide further detail of the basic kidney shaped implant 10. A male portion 108 slides with an opening 109 defined by side walls and a floor portion. The bioresorbable spacer 104 is disposed therebetween. As the upper and lower body portions 100, 103 exert loads on the bioresorbable spacer 104 via the loads on the vertebral bodies, it is not necessary to have a free sliding fit. In fact, it is only necessary that the male portion 108 slide within the opening or female portion 109 under load.

Within the lower portion 103, a shelf 110 is provided to provide a floor portion on which the bioresorbable spacer rests. The male portion 108 also includes a lower edge and face 108a that contacts the bioresorbable spacer 104 and maintains contact with it until the bioresorbable spacer 104 is fully resorbed. Thus, the present invention provides the two body portions 100, 103 with end plates that contact the end plates of the vertebral body and are interconnected relative to each other to allow for sliding motion therebetween. Although other hinge connections can be utilized, the present invention allows for the relative sliding motion between the body portions 100, 103 to allow movement therebetween as there is resorbtion of the resorbable spacer 104. This ability to reduce height of the device 10 in combination with the bone graft chamber providing a column of bone graft material contained therein for contact with each of the vertebral end plates, results in the bone graft load sharing mechanism of the present invention.

Figure 8:
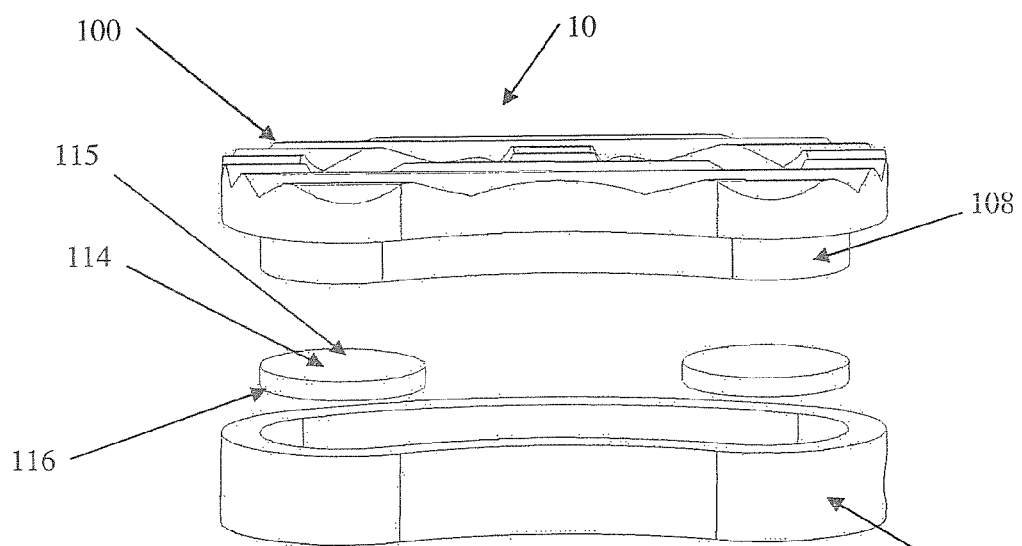
FIG. 8 is a side perspective view which is exploded showing a second embodiment of a bioresorbable disc spacer.

While the bioresorbable spacer 104 can be shaped to match the exact inside of the female portion of the lower section 103, as shown in FIG. 7, the bioresorbable spacer 104 can be more than one piece and of different shapes, such as shown in FIG. 8. In FIG. 8, the bioresorbable spacers 114 are round pads. Such pads 114 have an upper face 115 for contact with the upper section 100 and a lower face 116 for contact with a portion of the shelf 110 within the lower portion 103.

Figure 9:
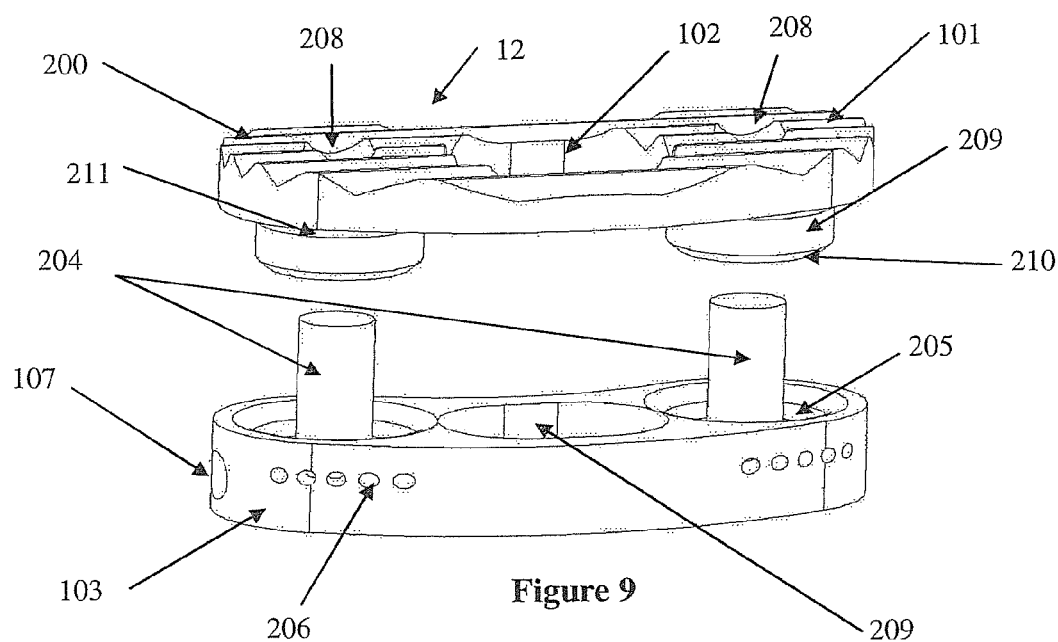
FIG. 9 is an exploded side perspective view showing aligning columns for use with various bioresorbable materials.

FIG. 9 shows the implant design modified to accept bioresorbable materials which are not as strong under compressive loads. In one variation shown in FIG. 9, the bioresorbable material is shaped into a ring 205 which is then placed over posts 204 thereby stabilizing the ring 205. The posts 204 slide within openings 208 in the upper section 100. The two sections 209 slide within cavities in the lower section 103, with the lower face of the two sections 209, represented by 210, in contact with the bioresorbable rings. A blend radius 211 is formed or machined into the transition between the section 209 and the upper body portion 100 to prevent stress risers when the two geometries meet. The posts 204 and the lower body portion 103 can be machined from one piece, such that the posts 204 provide additional guides for the upper body portion 100 to move relative to the lower body portion 103.

In a further embodiment, the posts are formed from a bioresorbable material, thus allowing the bioresorbable material to contact the vertebral bodies. The posts 204 can be formed from the same bioresorbable material as the ring, or molded as one unit, or a completely different bioresorbable material. In other words, various bioresorbable materials can be used for the different structures.

Additional holes 206 through the wall of the lower body portion 103 that extend into the inner cavity thereof, allow blood and fluids to contact the bioresorbable material contained therein and thereby permit the bioresorbable material to resorb over time. It is possible to use one lower section and two or more upper sections effectively acting as pistons, although it is desirable to keep the design simple and the number of components to a minimum. In other words, the upper and lower sections can function as a piston having an inner chamber containing the bioresorbable material. In any event, the structures provide for the height reducing mechanism of the present invention thereby placing constant load on the column of bone graft material.

In view of the above, if the implant device 10 is packed fully with bone graft material, the bone graft material packed into the graft chambers will take some load immediately. By allowing the two implant sections to move as the bioresorbable material is resorbed, the bone material always remains loaded, which creates better changes for fusion and better quality of bone strength and healing.

By using two implant sections 100, 103 that slide relative to one another, the amount of allowable motion can be readily controlled. The first implant section effectively acts as a base having a recess therein. The recess establishes a cavity with walls and a floor. The second implant section slides within this recess, having a geometry small enough to slide within the cavity and having a lower face. When this lower face contacts the floor of the cavity, the implant simply cannot move forward. It is possible to do this by creating a lip on the second implant that contacts the wall at some location on the first implant such that the floor and lower face never touch. This can also be done by creating a ledge within the cavity such that the lower face of the second implant contacts this ledge and stops. The present invention in accordance with this structure, provides a mechanism for controlling the axial sliding movement and the resulting decrease in height of the body portions 100, 103.

In order to insert the device 10 into the intervertebral space, an attachment mechanism or opening 107 is provided for engagement of an insertion instrument. Such engagement mechanisms can be threaded, such as shown 107a, a hole 107, which would accept an instrument with an expanding tip, a bayonet-type opening, or other attachment well known in the art.

FIGS. 10-18 show an alternative embodiment of the present invention as the implant device is shown in a rectangular shape represented generally at 14. Of course, the present invention is not restricted to either the kidney shape shown at 10 or the rectangular shape shown at 14. The device can be made round, vertebral body shape, or any other shape which fits the anatomy and surgical procedure.

As shown in FIGS. 10-18, the basic features of the present invention 14, as represented by the same numbers, are the same as FIGS. 1-9. Other features can be present in other shape variations. For example, for ease of insertion of a rectangular implant into the disc space, a radiused edge, 310, reduces the height of the implant at its edge and makes it easier to insert. A blend radius 310 breaks the sharp edge between the edge of the implant and its sides. It is also possible to use one longer opening 102 due to the length and shape of the implants. Optional holes or openings in the sides 206 allow for more body fluids to reach the bioresorbable spacer. Hence, timing of resorbtion can be controlled.

Figure 12:
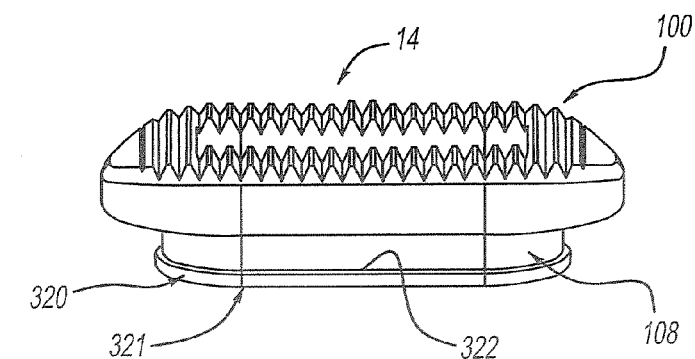
FIG. 12 is a perspective side exploded view of the rectangular embodiment of the present invention.
Figure 12:
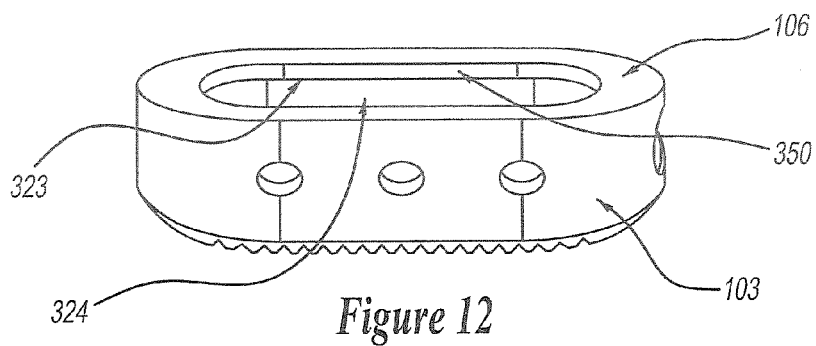
Figure 13:
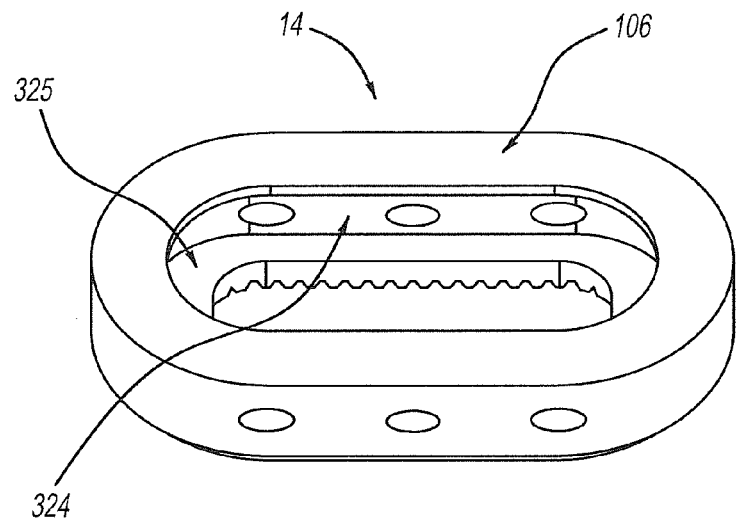
FIG. 13 is a top perspective view of the lower implant portion or base constructed in accordance with the present invention.
Figure 14:
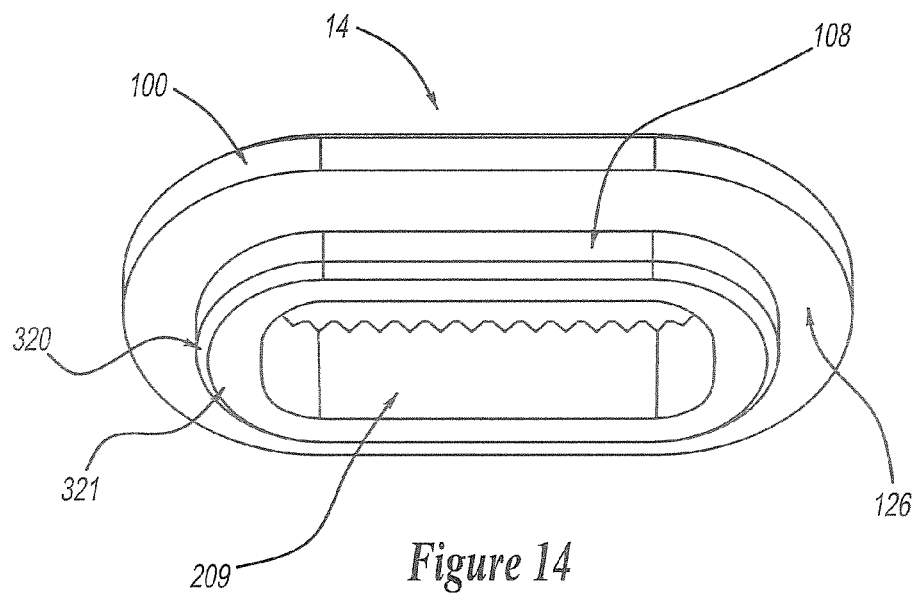
FIG. 14 is a bottom perspective view of the implant upper section.
Figure 15:
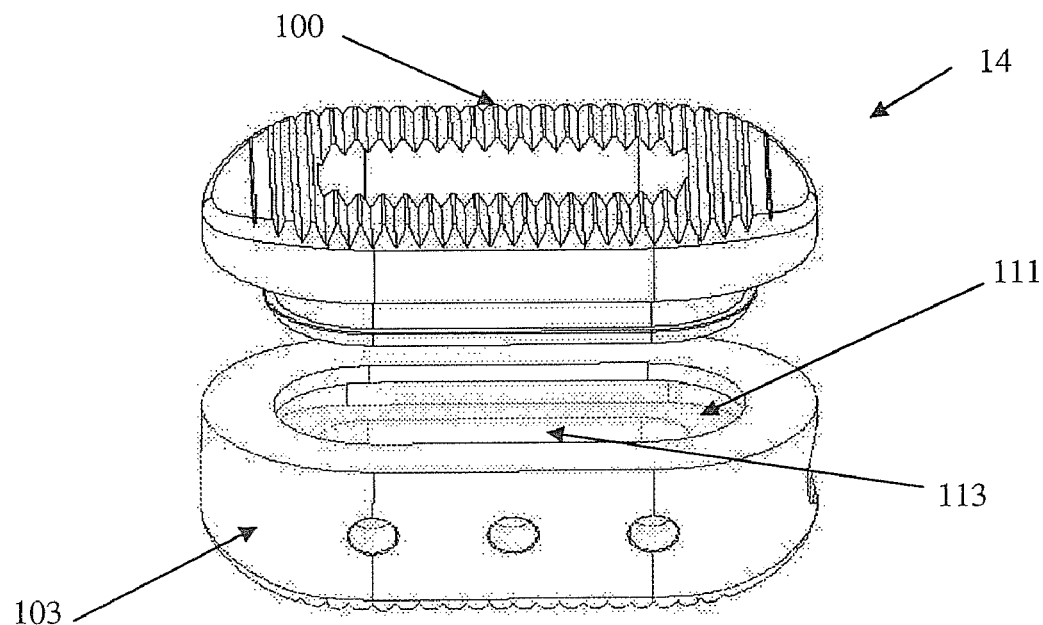
FIG. 15 is a perspective assembly view of the inventive implant.
Figure 16:
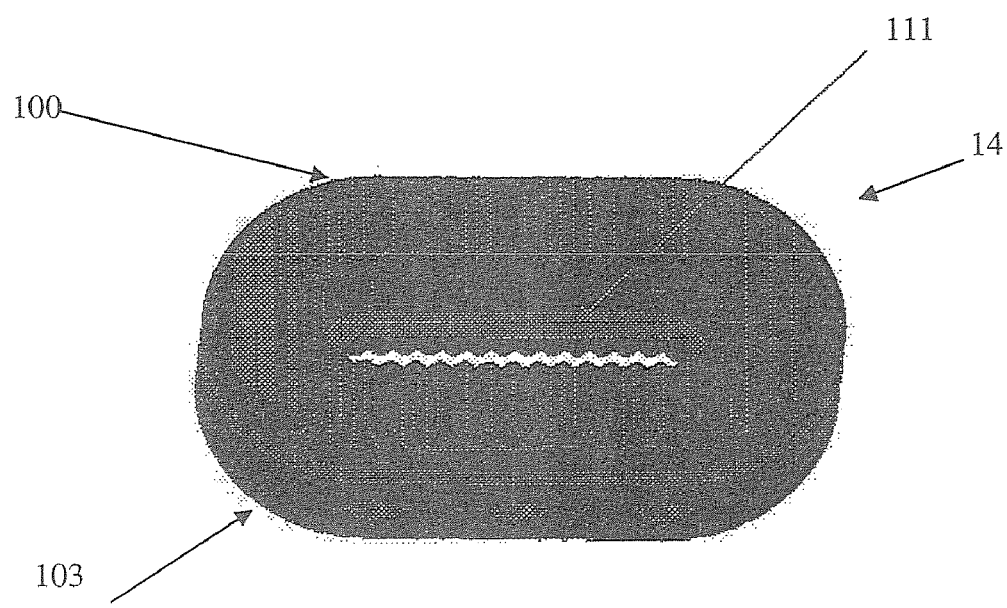
FIG. 16 is a shaded assembled implant.
Figure 17:
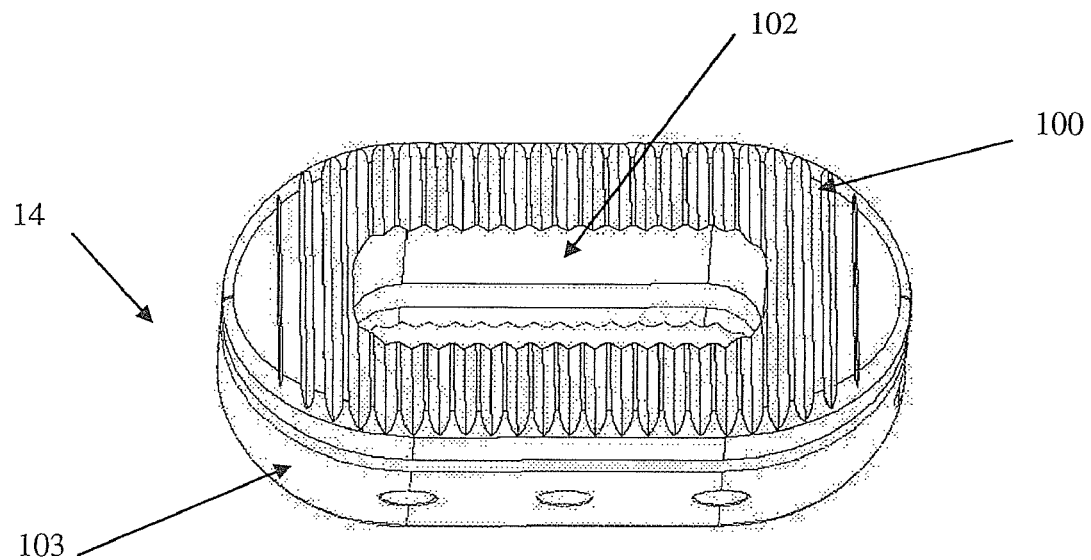
FIG. 17 is a top perspective view of the rectangular embodiment of the present invention.
Figure 18:
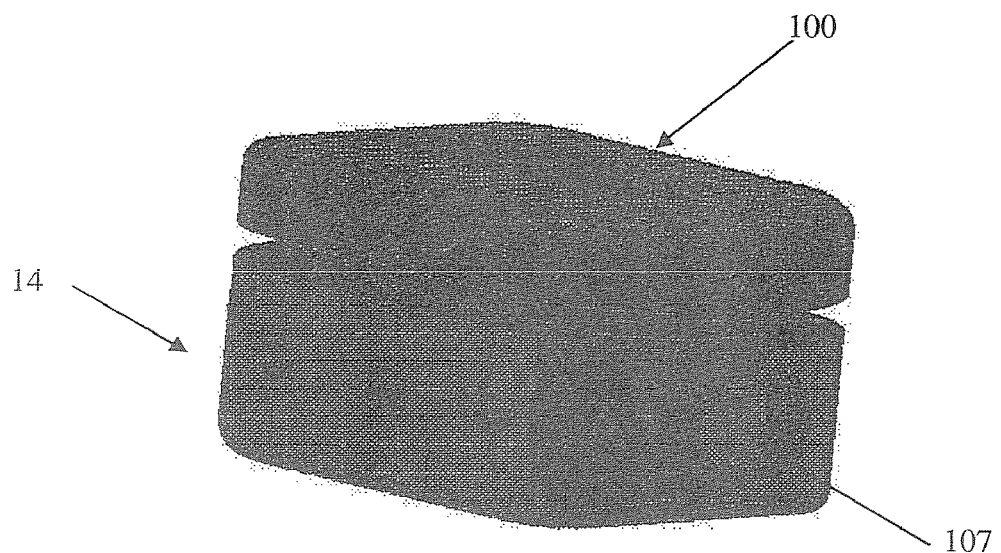
FIG. 18 is an assembly view shaded of the present implant invention.

FIG. 12 shows a detailed view of the upper and lower section of the implant 14. The upper section 100 has a lip portion 320 with an upper surface 332 and a lower surface 321. In general, the lip portion 320 is a chamfered surface for ease of inserting the male portion 108 into the lower section 103. The lower section 103 has a lip or ledge which extends inwardly away from the inner wall of the body of the lower section 103. This construction creates an opening 324 that is smaller than the inside cavity. Thus, when the upper section 100 is pressed downward against the lower portion 103, the upper section chamfer contacts the ledge inner surface 350. Additional force pushes the chamfer through the hole by using the elasticity of the material. Once through, the upper body portion 100 is locked within the lower section, as the lip 320 is under the lower surface of the ledge 323. It is also possible to create more features such as the sect of 320 and 321 to create multiple teeth. This creates a ratchet affect, such that the upper section male portion 108 is advanced further into the lower section opening 324 while sequential teeth catch the lower surface of the ledge 323. Thus, the device 10 locks into the new height locations and is prevented from being pulled apart once compressed from that specific height location.

The bioresorbable material as shown in the device 14 rests on the surface 325, with the upper section face 321 pressing against the bioresorbable material 111. The bioresorbable insert 111 can be made from one or more pieces, or one piece with a split through one side, such that it is capable of being compressed through the smaller opening and lip 320. The rate of resorbtion of the spacer and initial height are variables which can be readily controlled.

It is possible to supply multiple spacers according to patient needs and bone quality to increase or decrease the time to full resorbtion. In addition, certain materials and bioresorbable materials compress over time, or creep under stress. These materials can be used as well to maintain initial implant height while allowing for graft loading over time. The material used to form the upper and lower sections 100, 103, can be a polymer, such as PEEK, or any metal or ceramic.

While the present invention can be practiced as described above, it can be appreciated that the present invention can provide an insert device which decreases in height but not necessarily provides grafting. In other words, the present invention can be provided with the height reducing mechanism without the graft chambers. Likewise, the present invention can be provided without the height reducing function yet provided with sufficiently tightly packed bone graft material extending from end to end and exposed to the vertebral column such that the vertebral columns per se provide sufficient stress on the bone graft material, even though there is no height reducing mechanism.

In view of the above, it can be appreciated that the present invention broadly provides an inner body fusion device including the first body portion 100 including a first side having a first end plate surface for engaging an end plate of a first vertebral body and a second opposite side having a male portion extending therefrom, the male portion including the end surface thereof. The second body portion 103 includes a second end plate surface for engaging an opposing end plate of a second vertebral body, and also includes a cavity defined by a wall portion surrounding a floor portion for slidingly receiving the male portion therein and entrapping a bioresorbable material between the end surface and the floor portion. This construction provides a piston mechanism for entrapping the bioresorbable material therein while having a predetermined height which reduces as the bioresorbable material resorbs. Likewise, the device generally comprises a male member and female member for entrapping the bioresorbable material therebetween.

The present invention further generally provides a method of spacing apart opposing vertebral end plates by the surgeon inserting a spacer between opposing vertebral end plates and controlling reduction in height of the spacer during a healing process of a reconstructed vertebral space defined by the end plates. This is achieved by collapsing the internal chamber of the spacer to decrease the height of the spacer. Resorbtion of the bioresorbable material between the upper and lower body portions 100, 103 while being under load accomplish this result. This is accomplished by accessing body fluid into and out of the internal chamber to cause the resorbtion of the bioresorbable material and loss of the bioresorbable material from the internal chamber to collapse the internal chamber and decrease the height of the spacer. As discussed above, a column of bone graft material in the spacer is placed under load sharing conditions with the spacer as the spacer decreases in height. If the spacer completely collapses the internal chamber and the bone graft material fails to space apart the opposing vertebral end plates, the spacer itself prevents impingement of proximal nerves.

The present invention further generally provides a method of spacing apart opposing vertebral surfaces by entrapping a bioresorbable material within a piston body having a predetermined height, fixedly engaging the piston between opposing vertebral end plates, and reducing the height of the piston as their bioresorbable material resorbs. Likewise, the present invention provides a method of fusing together opposing intervertebral surfaces by implanting the body members 100, 103 between opposing vertebral surfaces, maintaining spacing between the opposing vertebral surfaces as the opposing vertebral surfaces place a load on the body, and on the body members 100, 103, and sharing the load between the body and bone graft material contained by the body. This method of sharing the load between the body members and the bone graft material novelly provides stress on the bone graft material thereby inducing remodeling. Thus, the present invention provides a model of remodeling the vertebral bone by containing a column of bone graft material in a body member having a reducible height while exposing ends of the column, inserting the body member between opposed vertebral end plates, and decreasing the height of the body member over time to load the bone graft material over time.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

The invention claimed is:

1. An interbody fusion device comprising:
body means for spacing apart opposing vertebral surfaces when said body means is implanted therebetween; and
bone graft load sharing means for sharing loads, placed on said body means by the opposing vertebral surfaces, between said body means and bone graft material contained by said body means, said bone graft load sharing means including height reducing means for decreasing a height of said body means over time and loading both said body means and the bone graft material over time, said height reducing means including a male portion of said body means in sliding and mating engagement with a female portion of said body means defining a chamber therebetween for containing a bioresorbable material therein, said height reducing means including a collapsible chamber within said body means, said collapsible chamber including an open condition for containing bioresorbable material therein and a collapsed condition in which said body means reduces height thereof, an insert of resorbable material being disposed in said chamber to initially support said chamber in said open condition.

2. The interbody fusion device of claim 1, wherein said body means include at least two body members, each of said body members including one of said male and female portions, said body members being interconnected by said female and male portions allowing axial movement relative to each of said body members.

3. The interbody fusion device of claim 2, wherein each of said body members includes end plate surfaces opposite either of said female and male portions for engaging an opposing end plate of a vertebral body.

4. The interbody fusion device of claim 3, wherein said end plate surfaces of said body members include gripping means for gripping the end plates of the opposing vertebral bodies and preventing sliding movement therebetween.

5. The interbody fusion device of claim 1, wherein said insert is selected from the group of bioresorbable materials including polyesters, poly (amino acids), polyanhydrides, polyorthoesters, polyurethanes, polycarbonates and copolyesters of $\Sigma$-caprolactone, trimethylene carbonate, and para-dioxanone.

6. The interbody fusion device of claim 5, wherein said polyester is selected from the group of homopolymers and copolymers of poly(lactic acid) (PLLA) and poly(glycolic acid) (PLGA).

7. The interbody fusion device of claim 1, wherein said body means is kidney shaped.

8. The interbody fusion device of claim 1, wherein said body means is rectangular shaped.

9. The interbody fusion device of claim 1, wherein said bone graft load sharing means further includes at least one bone graft chamber for containing bone graft material therein, said chamber including openings in each of said end plate surfaces allowing for contact of the bone graft material contained therein with the vertebral end plates, said bone graft chamber defining a column extending axially through said body means whereby bone graft material fully packed into said bone graft chamber takes load on when said body means is disposed between the opposing vertebral end plates.

10. An interbody fusion device comprising:
body means for spacing apart opposing vertebral surfaces when said body means is implanted therebetween;
said body means including at least two body members, each of said body members including one of said male and female portions, said body members being interconnected by said female and male portions allowing axial movement relative to each of said body members; and
bone graft load sharing means for sharing loads, placed on said body means by the opposing vertebral surfaces, between said body means and bone graft material contained by said body means, said bone graft load sharing means including height reducing means for decreasing a height of said body means over time and loading both said body means and the bone graft material over time, said height reducing means including a male portion of said body means in sliding and mating engagement with a female portion of said body means defining a chamber therebetween for containing a bioresorbable material therein each of said body members includes end plate surfaces opposite either of said female and male portions for engaging an opposing end plate of a vertebral body, said bone graft load sharing means further including at least one bone graft chamber for containing bone graft material therein, said chamber including openings in each of said end plate surfaces allowing for contact of the bone graft material contained therein with the vertebral end plates, said bone graft chamber defining a column extending axially through said body means whereby bone graft material fully packed into said bone graft chamber takes on load when said body means is disposed between the opposing vertebral end plates, said body means including at least one port extending from an external surface of said body member containing said chamber, which contains the bioresorbable material for allowing body fluids to contact and cause resorbtion of said bioresorbable material and effect a continuous decrease in height of said body means effecting a continuous load on the bone graft material contained within said bone graft chambers.

11. The interbody fusion device of claim 10, wherein said body means further includes axial sliding control means for controlling the amount of axial sliding and resulting decrease in height of said body means.

12. The interbody fusion device of claim 11, wherein said female portion includes wall portions surrounding a floor portion defining an axially extending recess and said male portion having an end surface, said end surface, wall portions, and floor defining said chamber for containing the bioresorbable material.

13. The interbody fusion device of claim 12, wherein said male portion includes a neck portion extending from a base portion and including said end surface at a distal end thereof, said end surface bottoming out against said floor and defining said axial sliding control means.

14. The interbody fusion device of claim 12, wherein said recess includes a ledge portion extending radially inwardly from said wall portions and spaced from said floor portion for abutting contact with said end surface of said male portion defining said axial sliding control means.

15. The interbody fusion device of claim 13, wherein said neck portion includes a lip extending radially outwardly therefrom and spaced axially from said end surface for abutting against a ledge of said recess defining said axial sliding control means.

* * * * *